United States Patent
Lee et al.

(10) Patent No.: US 11,832,894 B2
(45) Date of Patent: *Dec. 5, 2023

(54) ADJUSTABLE LENGTH MEDICAL INSTRUMENT ASSEMBLY WITH LOCALIZATION ELEMENTS FOR TRACKING MEDICAL INSTRUMENT EXTENSION

(71) Applicant: Veran Medical Technologies, Inc., St. Louis, MO (US)

(72) Inventors: Christopher Lee, St. Louis, MO (US); Mark Hunter, St. Louis, MO (US); Troy L. Holsing, Golden, CO (US)

(73) Assignee: Veran Medical Technologies, Inc., St. Louis, MO (US)

( * ) Notice: Subject to any disclaimer, the term of this patent is extended or adjusted under 35 U.S.C. 154(b) by 515 days.

This patent is subject to a terminal disclaimer.

(21) Appl. No.: 17/089,832

(22) Filed: Nov. 5, 2020

(65) Prior Publication Data

US 2021/0068904 A1 Mar. 11, 2021

Related U.S. Application Data

(63) Continuation of application No. 16/142,589, filed on Sep. 26, 2018, now Pat. No. 10,835,324, which is a
(Continued)

(51) Int. Cl.
*A61B 5/00* (2006.01)
*A61B 34/20* (2016.01)
(Continued)

(52) U.S. Cl.
CPC .......... *A61B 34/20* (2016.02); *A61B 10/0233* (2013.01); *A61B 17/00234* (2013.01);
(Continued)

(58) Field of Classification Search
CPC . A61B 90/17; A61B 6/547; A61B 2034/2051; A61B 2034/2072
See application file for complete search history.

(56) References Cited

U.S. PATENT DOCUMENTS

| 6,770,066 B1 | 8/2004 | Weaver |
| 7,056,319 B2 | 6/2006 | Aliperti |

(Continued)

OTHER PUBLICATIONS

PCT, International Search Report for PCT/US2016/031894, dated Aug. 17, 2016, 5 pages, dated Aug. 17, 2016.
(Continued)

*Primary Examiner* — Rajeev P Siripurapu
(74) *Attorney, Agent, or Firm* — Forsgren Fisher McCalmont DeMarea Tysver LLP; James M. Urzedowski; Daniel A. Tysver

(57) ABSTRACT

A medical instrument assembly including a handle assembly having a first handle portion and a second handle portion proximate the second end, wherein the second handle portion is slidably engaged with the first handle portion. A first localization element is attached to the first handle portion and a second localization element is attached to the second handle portion. A medical instrument is mechanically coupled to the second handle portion and a translation of the second handle portion with respect to the first handle portion causes a coincident and coextensive translation of the medical instrument. The amount of translation of the medical instrument is adapted to be determined by calculating the distance between the first localization element and the second localization element. The first and second localization elements may be electromagnetic sensors which positions may be determined by a navigation system.

11 Claims, 11 Drawing Sheets

Related U.S. Application Data continuation of application No. 14/708,449, filed on May 11, 2015, now Pat. No. 10,111,715.

(51) Int. Cl.
| | |
|---|---|
| *A61B 17/00* | (2006.01) |
| *A61B 90/10* | (2016.01) |
| *A61B 90/00* | (2016.01) |
| *A61B 10/02* | (2006.01) |
| *A61B 17/34* | (2006.01) |
| *A61B 10/06* | (2006.01) |
| *A61B 10/04* | (2006.01) |
| *A61B 17/06* | (2006.01) |

(52) U.S. Cl.
CPC ...... *A61B 17/3403* (2013.01); *A61B 17/3478* (2013.01); *A61B 90/10* (2016.02); *A61B 90/361* (2016.02); *A61B 90/37* (2016.02); *A61B 10/0283* (2013.01); *A61B 10/06* (2013.01); *A61B 2010/0216* (2013.01); *A61B 2010/045* (2013.01); *A61B 2017/003* (2013.01); *A61B 2017/00309* (2013.01); *A61B 2017/00331* (2013.01); *A61B 2017/00336* (2013.01); *A61B 2017/00424* (2013.01); *A61B 2017/00809* (2013.01); *A61B 2017/00867* (2013.01); *A61B 2017/06095* (2013.01); *A61B 2034/2051* (2016.02); *A61B 2090/0811* (2016.02); *A61B 2090/3966* (2016.02)

(56) References Cited

U.S. PATENT DOCUMENTS

| | | | |
|---|---|---|---|
| 7,419,501 | B2 | 9/2008 | Chiu |
| 8,632,461 | B2 | 1/2014 | Glossop |
| 10,111,715 | B2* | 10/2018 | Lee .................. A61B 90/361 |
| 10,835,324 | B2* | 11/2020 | Lee .................. A61B 90/10 |
| 2004/0097806 | A1* | 5/2004 | Hunter ............ A61B 1/00071 600/434 |
| 2007/0032723 | A1 | 2/2007 | Glossop |
| 2007/0055128 | A1* | 3/2007 | Glossop .............. A61B 1/018 600/407 |
| 2009/0118673 | A1 | 5/2009 | Creed |
| 2010/0036238 | A1* | 2/2010 | Neidert ................ A61B 5/06 600/424 |
| 2010/0312141 | A1 | 12/2010 | Keast |
| 2013/0225997 | A1* | 8/2013 | Dillard ............ A61B 10/0233 29/896.9 |
| 2014/0275991 | A1 | 9/2014 | Potter |
| 2015/0012008 | A1 | 1/2015 | Mcweeney |
| 2015/0305770 | A1* | 10/2015 | Fill .................. A61B 17/3478 600/235 |

OTHER PUBLICATIONS

Jun. 2, 2020 USPTO Office Action (U.S. Appl. No. 16/142,589)—Our Matter 5791.

* cited by examiner

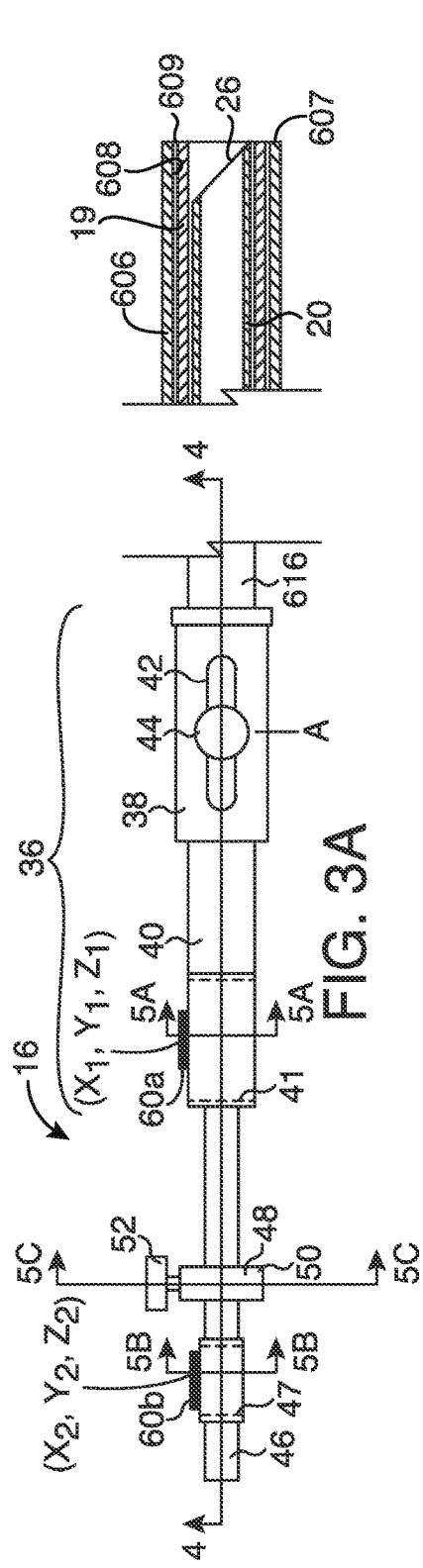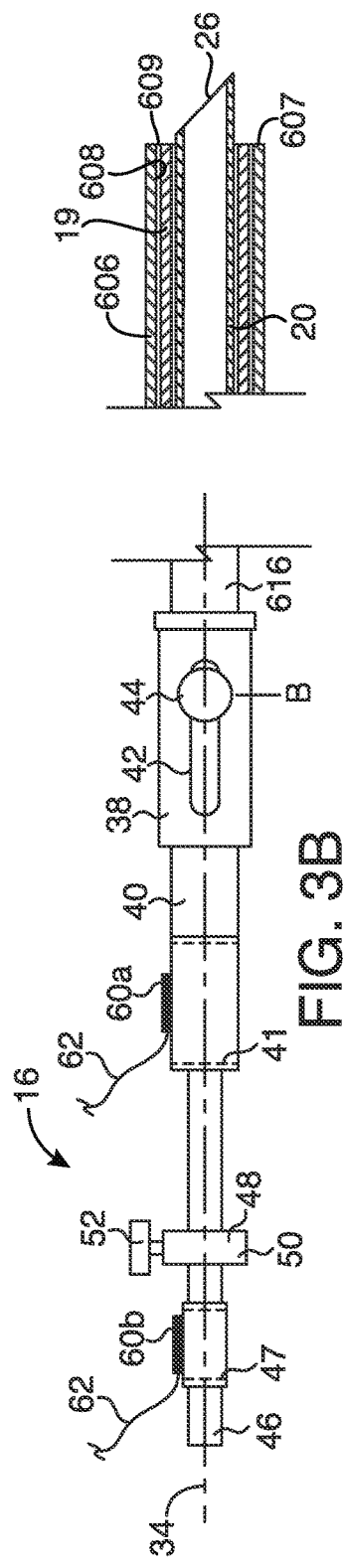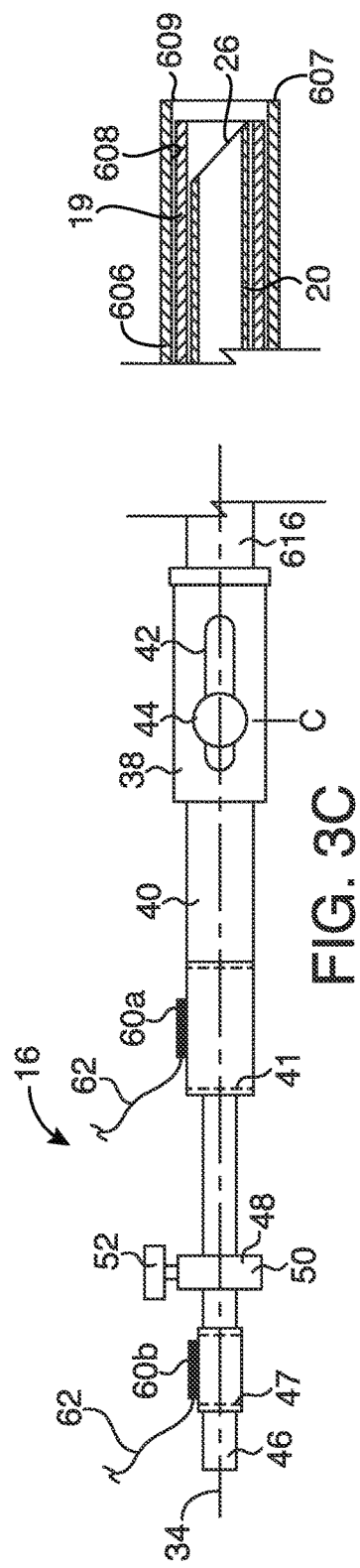

ADJUSTABLE LENGTH MEDICAL INSTRUMENT ASSEMBLY WITH LOCALIZATION ELEMENTS FOR TRACKING MEDICAL INSTRUMENT EXTENSION

FIELD OF THE INVENTION

This invention relates generally to medical instruments and systems and, more particularly, to apparatuses and systems associated with a range of medical procedures for detecting, sampling, staging and/or treating target tissues in the lungs of a patient.

BACKGROUND OF THE INVENTION

Image guided surgery (IGS), also known as image guided intervention (IGI), enhances a physician's ability to locate instruments proximate to and/or within anatomy during a medical procedure. IGS can include 2-dimensional (2D), 3-dimensional (3D), and 4-dimensional (4D) applications. The fourth dimension of IGS can include multiple parameters either individually or together such as time, motion, electrical signals, pressure, airflow, blood flow, respiration, heartbeat, and other patient measured parameters.

Navigation systems are used with image guided surgery to track the positions of the medical instruments in the body of a patient. The positions can be superimposed on 2D, 3D and/or 4D images of the body of the patient. The images are usually pre-acquired x-ray, computed tomography (CT), ultrasound, and/or magnetic resonance imaging (Mill) images. Superimposing the medical instruments on the images assists a physician or other user in navigating the medical instrument and/or performing a medical procedure.

Although significant improvements have been made in these fields, a need remains for improved medical instruments, systems, and procedures for visualizing, accessing, locating, sampling and manipulating a target tissue.

SUMMARY OF THE INVENTION

One aspect of the invention is directed to a medical instrument assembly comprising a handle assembly having a first end and a second end, wherein the handle assembly comprises a first handle portion proximate the first end and a second handle portion proximate the second end. The second handle portion is slidably engaged with the first handle portion. The medical instrument assembly further includes a first localization element attached to the first handle portion and a second localization element attached to the second handle portion. The medical instrument assembly further includes a medical instrument having a proximal end and a distal end, wherein the proximal end is mechanically coupled to the second handle portion. A translation of the second handle portion with respect to the first handle portion causes a coincident and coextensive translation of the medical instrument. The amount of translation of the medical instrument is adapted to be determined by calculating the distance between the first localization element and the second localization element.

Another aspect of the invention is directed to an adjustable length medical instrument assembly comprising a handle assembly having a first end and a second end, wherein the handle assembly comprises an adjustment mechanism proximate the first end and an actuation handle proximate the second end. The adjustment mechanism includes an adjustment collar and an adjustment handle slidably engaged with the adjustment collar. The actuation handle is slidably engaged with the adjustment handle. The adjustable length medical instrument assembly further includes a first localization element attached to the adjustment mechanism and a second localization element attached to the actuation handle. The adjustable length medical instrument assembly further includes a medical instrument having a proximal end and a distal end, wherein the proximal end is mechanically coupled to the actuation handle. A translation of actuation handle with respect to the adjustment mechanism causes a coincident and coextensive translation of the medical instrument. The amount of translation of the medical instrument is adapted to be determined by calculating the distance between the first localization element and the second localization element.

Another aspect of the invention is directed to an adjustable length medical instrument assembly comprising a handle assembly having a first end and a second end, wherein the handle assembly comprises an adjustment mechanism proximate the first end and an actuation handle proximate the second end. The adjustment mechanism includes an adjustment collar and an adjustment handle slidably engaged with the adjustment collar. The actuation handle is slidably engaged with the adjustment handle. The adjustable length medical instrument assembly further includes a first localization element attached to the adjustment handle and a second localization element attached to the actuation handle. The adjustable length medical instrument assembly further includes a medical instrument having a proximal end and a distal end, wherein the proximal end is mechanically coupled to the actuation handle. A translation of actuation handle with respect to the adjustment mechanism causes a coincident and coextensive translation of the medical instrument. The amount of translation of the medical instrument is adapted to be determined by calculating the distance between the first localization element and the second localization element.

Yet another aspect of the invention is directed to a system for tracking the translation of a medical instrument comprising a catheter, a medical instrument assembly, and a navigation system. The catheter comprises an elongate flexible shaft having a proximal end portion comprising a port, an opposite distal end portion terminating in a tip, and a working channel extending from the port to an exit proximate the tip. The medical instrument comprises a handle assembly having a first end and a second end, the handle assembly comprising a first handle portion proximate the first end and a second handle portion proximate the second end, wherein the second handle portion is slidably engaged with the first handle portion. The medical instrument assembly further includes a first localization element attached to the first handle portion and a second localization element attached to the second handle portion. The medical instrument assembly further includes a medical instrument having a proximal end and a distal end, wherein the proximal end is mechanically coupled to the second handle portion. At least a portion of the medical instrument assembly is adapted to be inserted into the working channel of the catheter. A translation of the second handle portion with respect to the first handle portion causes a coincident and coextensive translation of the medical instrument. The navigation system is adapted to determine a first position of the first localization element and a second position of the second localization element, and is adapted to determine the amount of translation of the medical instrument by calculating the distance between the first localization element and the second localization element based on the first position of the first localization element and the second position of the second localization element.

In various aspects of the invention the first handle portion and the second handle portion of the medical instrument assembly each comprise a groove in which the first and second localization elements, respectively, are adapted to be releasably retained.

In various aspects of the invention the first and second localization elements are adapted to be coupled to a processor and adapted to send to the processor information associated with a first position in three-dimensional space of the first localization element and information associated with a second position in three-dimensional space of the second localization element.

In various aspects of the invention the amount of translation of the medical instrument is adapted to be determined by calculating the distance between the first position of the first localization element and the second position of the second localization element.

In various aspects of the invention the first and second localization elements are adapted to produce outputs corresponding to the positions of the first and second localization elements. The outputs of the first and second localization elements are adapted to be received by a navigation system which is adapted to determine the amount of translation of the medical instrument by calculating the distance between the first localization element and the second localization element. The calculated distance is based on the outputs received from the first and second localization elements.

In various aspects of the invention the first and second localization elements are electromagnetic sensors.

In various aspects of the invention the output of the first and second localization elements is generated using an electromagnetic field generator.

BRIEF DESCRIPTION OF THE SEVERAL VIEW OF THE DRAWINGS

These and other features, aspects and advantages of the invention will become more fully apparent from the following detailed description, appended claims, and accompanying drawings, wherein the drawings illustrate features in accordance with exemplary embodiments of the invention, and wherein:

FIG. 3A is a side view of an adjustable length medical instrument assembly and a section view of a distal end portion of the adjustable length medical instrument assembly inserted into and connected with a catheter, wherein a medical instrument is at a desired nominal position according to the first embodiment of the invention;

FIG. 3B is a side view of an adjustable length medical instrument assembly and a section view of a distal end portion of the adjustable length medical instrument assembly inserted into and connected with a catheter, wherein a medical instrument is at an extended position according to the first embodiment of the invention;

FIG. 3C is a side view of an adjustable length medical instrument assembly and a section view of a distal end portion of the adjustable length medical instrument assembly inserted into and connected with a catheter, wherein a medical instrument is at a retracted position according to the first embodiment of the invention;

Figure 5A:
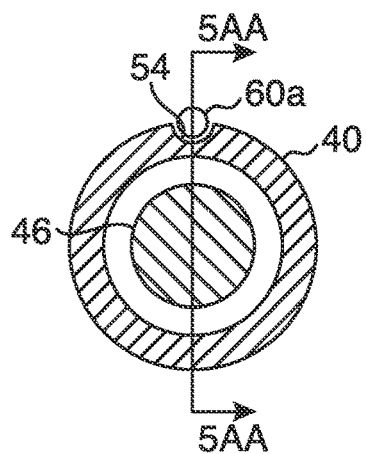
FIG. 5A is a section view of a portion of an adjustable length medical instrument assembly showing the attachment of a first localization element to an adjustment handle of the adjustable length medical instrument assembly according to the first embodiment of the invention.
Figure 5A:
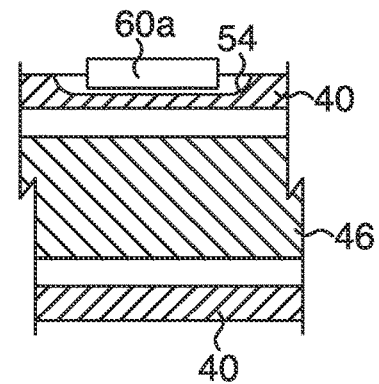
Figure 5B:
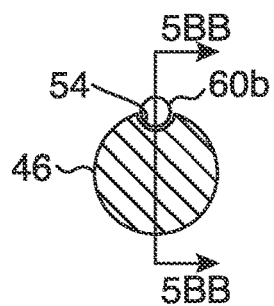
Figure 5B:
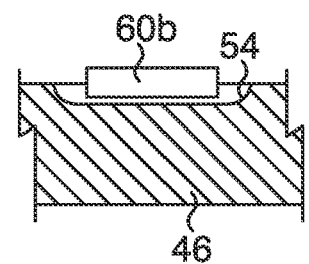
Figure 5C:
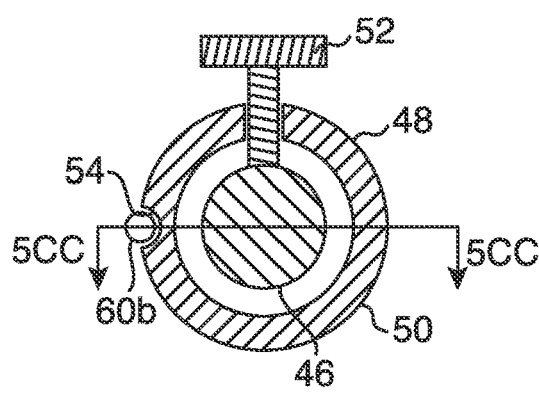
Figure 5C:
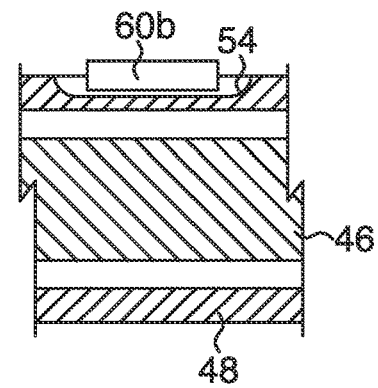
Figure 6:
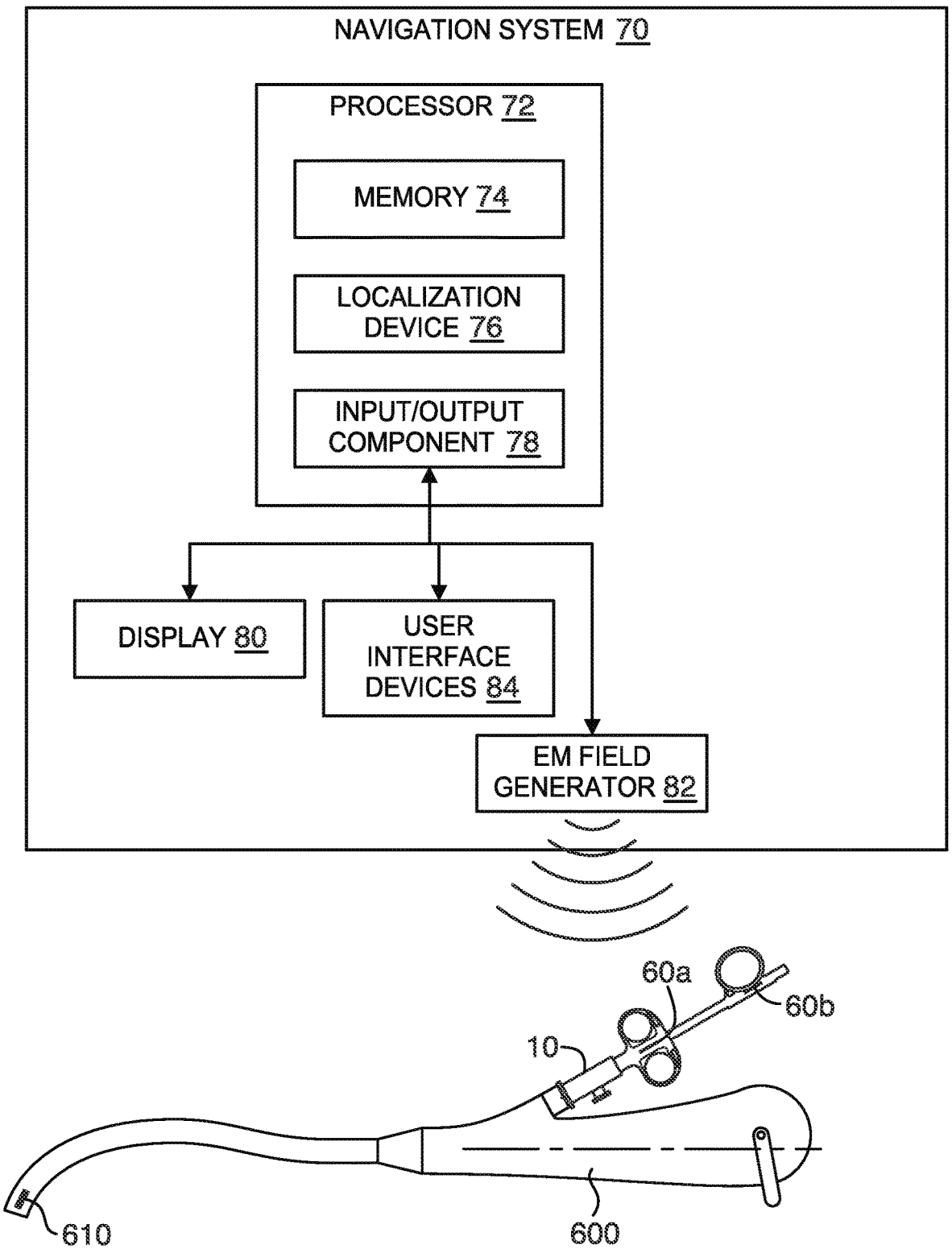
Figure 7:
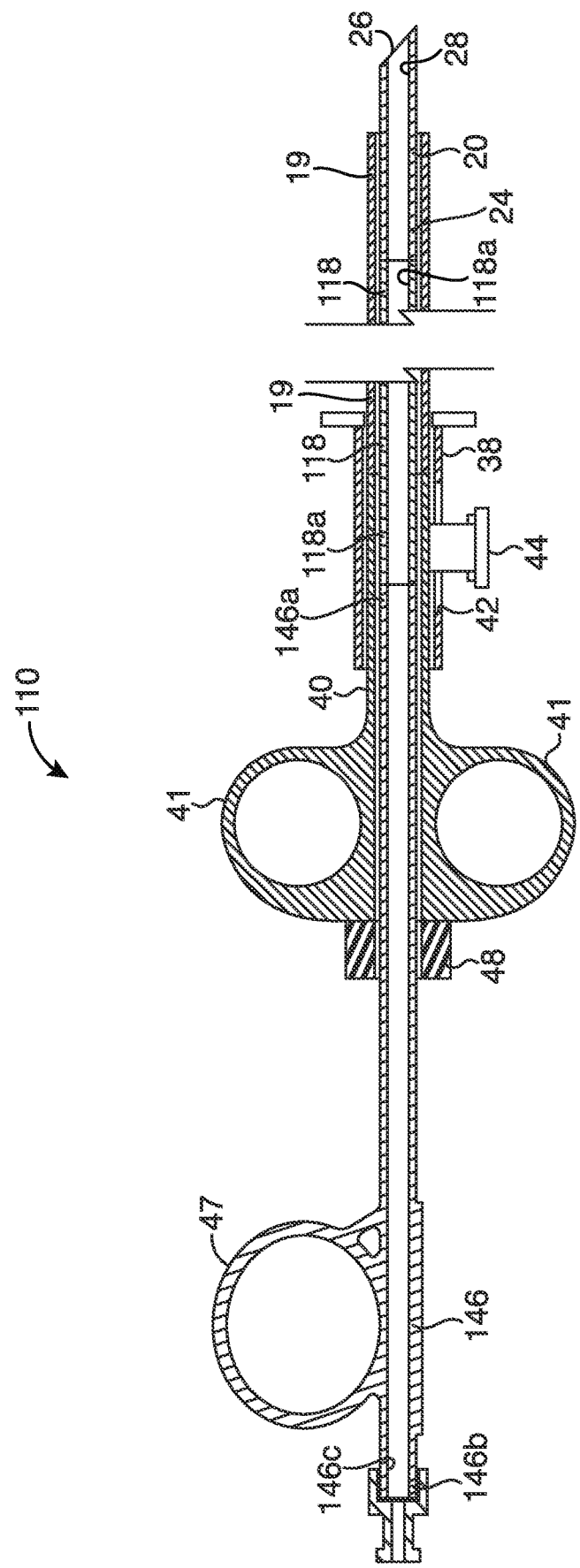
Figure 8:
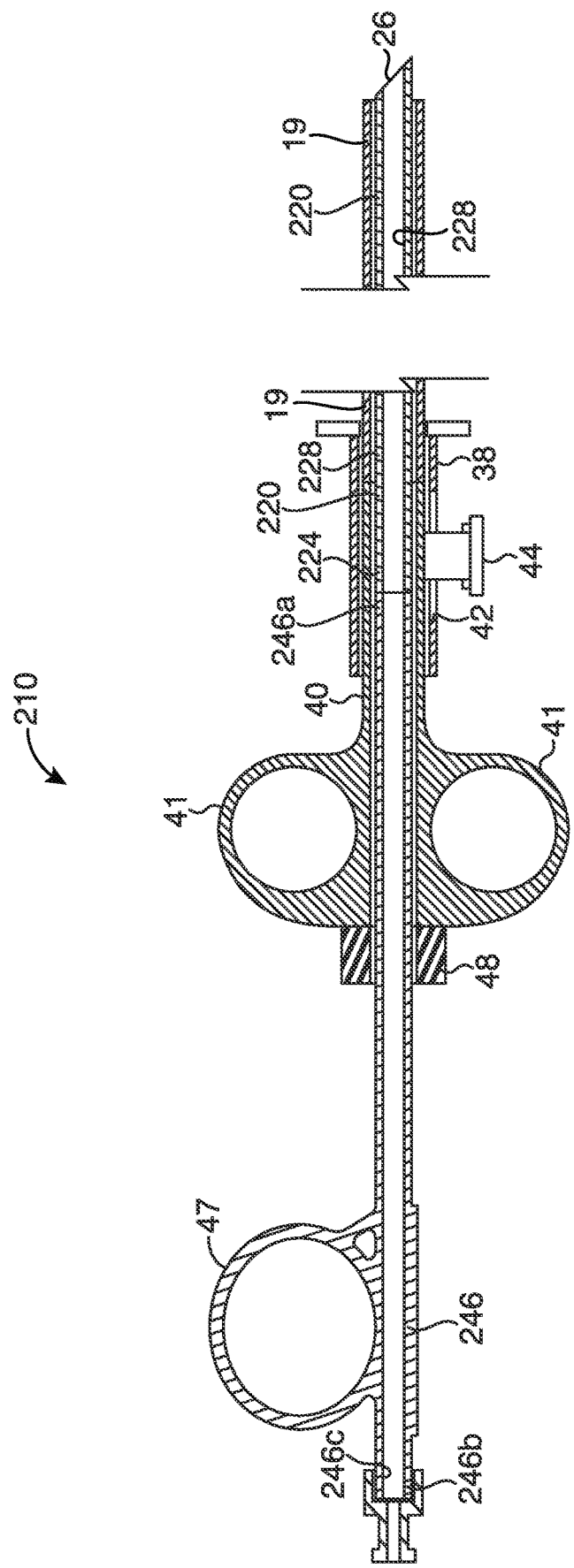
Figure 9A:
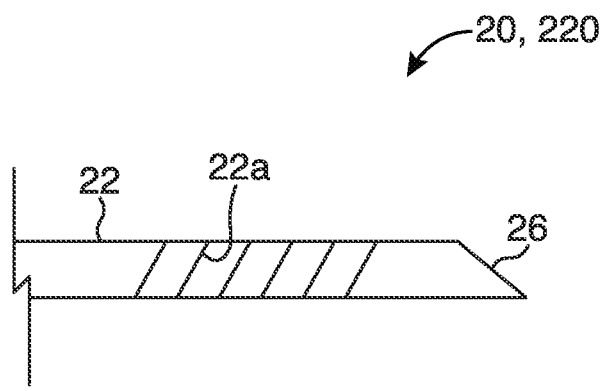
Figure 9B:
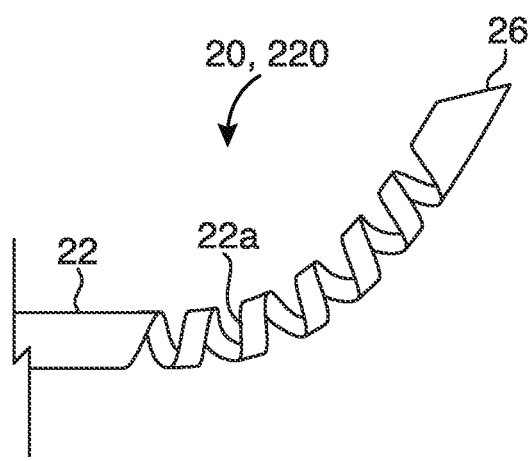
Figure 10A:
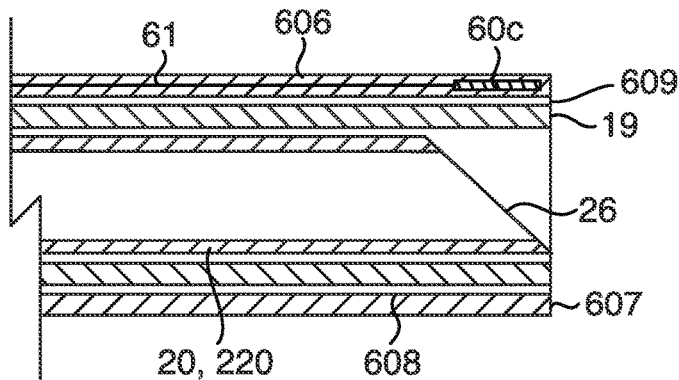
Figure 10B:
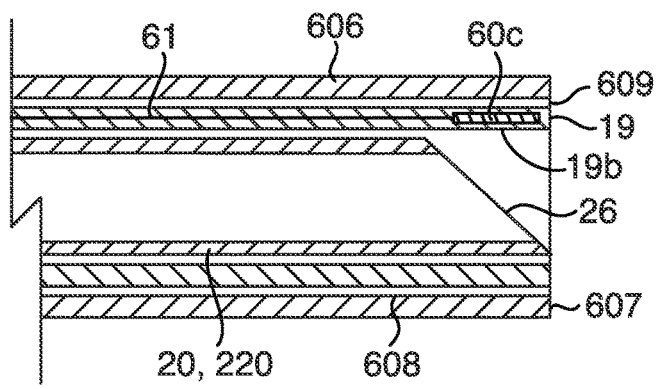
Figure 10C:
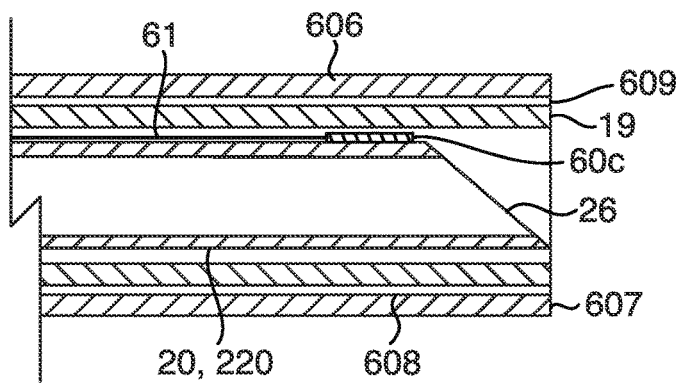
Figure 10D:
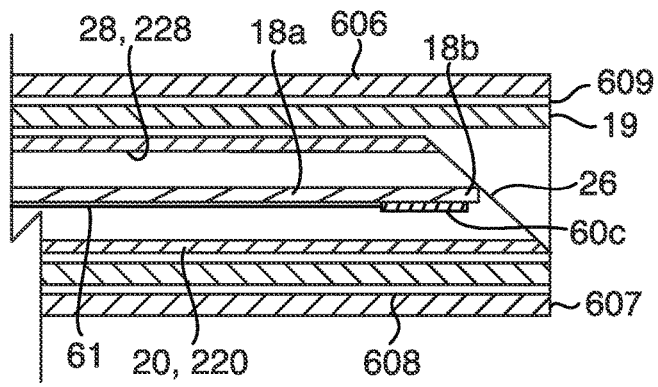
Figure 11A:
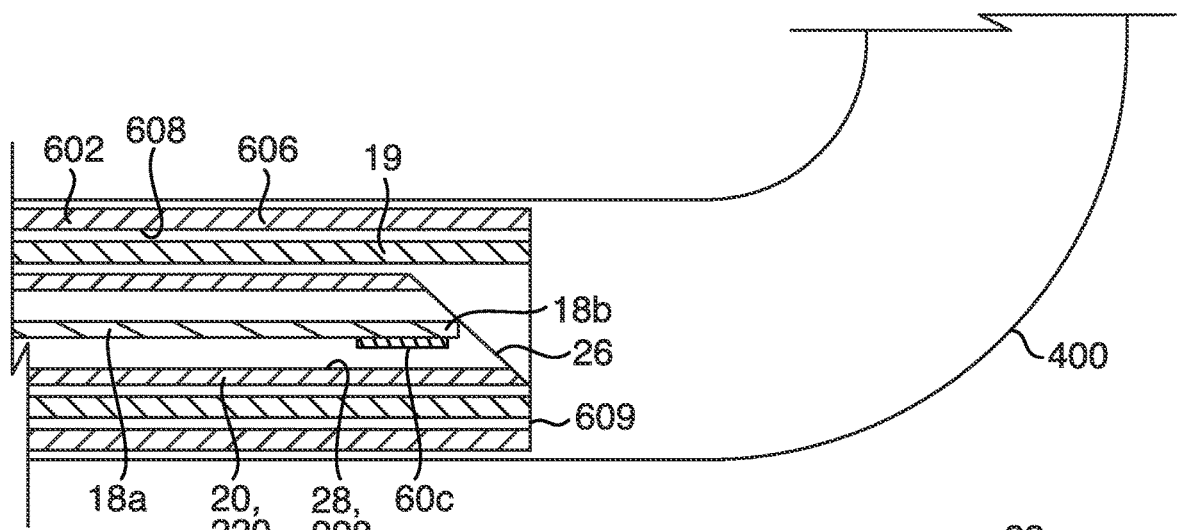
Figure 11B:
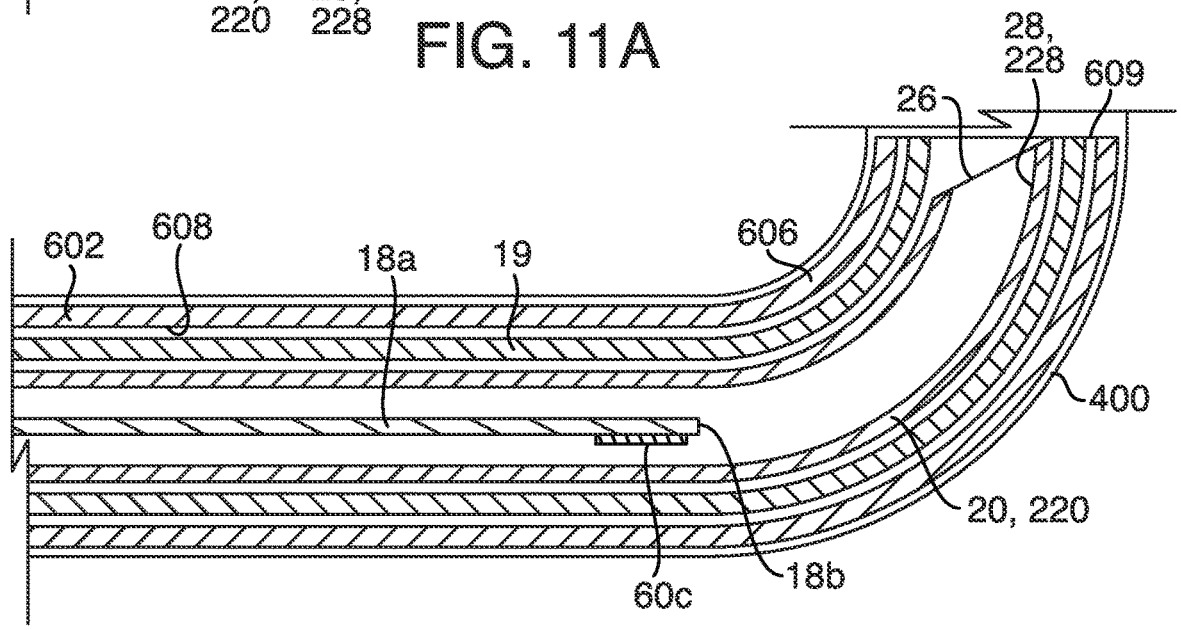
Figure 11C:
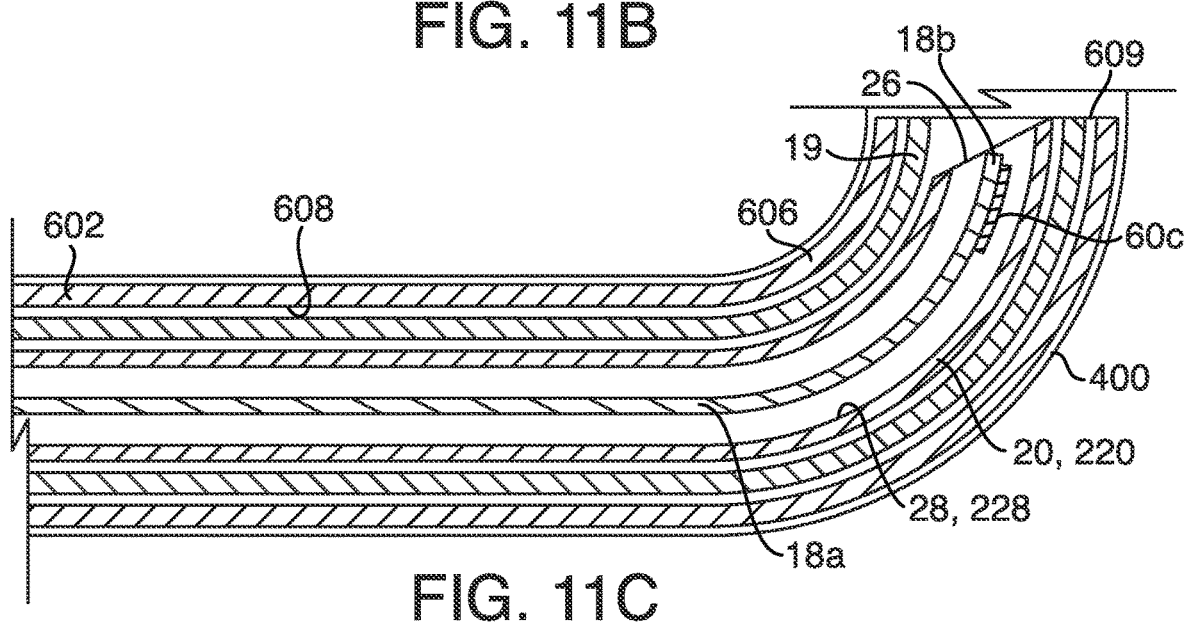

FIG. 5AA is a right section view of FIG. 5A showing the attachment of a first localization element to an adjustment handle of the adjustable length medical instrument assembly according to the first embodiment of the invention;

FIG. 5B is a section view of a portion of an adjustable length medical instrument assembly showing the attachment of a second localization element to an actuation handle of the adjustable length medical instrument assembly according to the first embodiment of the invention;

FIG. 5BB is a right section view of FIG. 5B showing the attachment of a second localization element to an actuation handle of the adjustable length medical instrument assembly according to the first embodiment of the invention;

FIG. 5C is a section view of a portion of an adjustable length medical instrument assembly showing the optional attachment of a second localization element to a stroke regulator of the adjustable length medical instrument assembly according to an embodiment of the invention;

FIG. 5CC is a right section view of FIG. 5C showing the optional attachment of a second localization element to a stroke regulator of the adjustable length medical instrument assembly according to an embodiment of the invention;

FIG. 6 is a schematic representation of a navigation system for use with the adjustable length medical instrument assembly according to the first embodiment of the invention;

FIG. 7 is a section view of a proximal end portion of an adjustable length medical instrument assembly and a section view of a distal end portion of the adjustable length medical instrument assembly, wherein the actuation handle of the adjustable length medical instrument assembly is actuated to extend the medical instrument according to a second embodiment of the invention;

FIG. 8 is a section view of a proximal end portion of an adjustable length medical instrument assembly and a section view of a distal end portion of the adjustable length medical instrument assembly, wherein the actuation handle of the adjustable length medical instrument assembly is actuated to extend the medical instrument according to a third embodiment of the invention;

FIG. 9A is a side view of a needle having a population of cuts to increase the flexibility of the needle according to an embodiment of the invention;

FIG. 9B is a side view showing the needle of FIG. 9A bent according to an embodiment of the invention;

FIG. 10A is a section view of a distal end portion of the adjustable length medical instrument assembly and the distal end portion of the elongate flexible shaft of the catheter, having a third localization element on or in the distal end portion of the elongate flexible shaft of the catheter according to an embodiment of the invention;

FIG. 10B is a section view of a distal end portion of the adjustable length medical instrument assembly and the distal end portion of the elongate flexible shaft of the catheter, having a third localization element on or in the distal end portion of the sheath of the adjustable length medical instrument assembly according to an embodiment of the invention;

FIG. 10C is a section view of a distal end portion of the adjustable length medical instrument assembly and the distal end portion of the elongate flexible shaft of the catheter, having a third localization element on or in the needle of the adjustable length medical instrument assembly proximate the tissue piercing distal end portion of the needle according to an embodiment of the invention;

FIG. 10D is a section view of a distal end portion of the adjustable length medical instrument assembly and the distal end portion of the elongate flexible shaft of the catheter, having a third localization element on or in a flexible guidewire inserted in a lumen of the needle of the adjustable length medical instrument assembly according to an embodiment of the invention;

FIG. 11A is a section view of a distal end portion of the adjustable length medical instrument assembly and the distal end portion of the elongate flexible shaft of the catheter, wherein a third localization element is on or in a flexible guidewire inserted in a lumen of the needle of the adjustable length medical instrument assembly, wherein the distal end of the flexible guidewire is proximate the tissue piercing distal end portion of the needle as the catheter is being navigated in an airway according to the embodiment of the invention shown in FIG. 10D;

FIG. 11B is a section view of a distal end portion of the adjustable length medical instrument assembly and the distal end portion of the elongate flexible shaft of the catheter, wherein a third localization element is on or in a flexible guidewire inserted in a lumen of the needle of the adjustable length medical instrument assembly, wherein the distal end of the flexible guidewire is partially retracted from the tissue piercing distal end portion of the needle as the catheter is being navigated in an airway according to the embodiment of the invention shown in FIG. 10D; and FIG. 11C is a section view of an end portion of the adjustable length medical instrument assembly and the distal end portion of the elongate flexible shaft of the catheter, wherein a third localization element is on or in a flexible guidewire inserted in a lumen of the needle of the adjustable length medical instrument assembly, wherein the distal end of the flexible guidewire is proximate the tissue piercing distal end portion of the needle as catheter is being navigated in an airway according to the embodiment of the invention shown in FIG. 10D.

Like reference numerals indicate corresponding parts throughout the several views of the various drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. All numbers expressing measurements and so forth used in the specification and claims are to be understood as being modified in all instances by the term "about." It should also be noted that any references herein to front and back, right and left, top and bottom and upper and lower are intended for convenience of description, not to limit an invention disclosed herein or its components to any one positional or spatial orientation.

With reference to FIGS. 1-6 certain principal components of one embodiment of an adjustable length medical instrument assembly 10 having localization elements for tracking the extension of a medical instrument attached to adjustable length medical instrument assembly 10 are described. Adjustable length medical instrument assembly 10 comprises a handle assembly 16 at a proximal end 12 of adjustable length medical instrument assembly 10, a medical instrument, preferably needle 20, at the distal end 14 of adjustable length medical instrument assembly 10, and a flexible guidewire 18 attached to needle 20 and extending toward and affixed to adjustable length medical instrument assembly 10. Needle 20 includes an outer wall 22 extending from a proximal end 24 to a tissue piercing distal end 26. Outer wall 22 defines a lumen 28 which extends at least partially from tissue piercing distal end 26 to proximal end 24. Flexible guidewire 18 is attached to proximal end 24 of needle 20. As described in greater detail elsewhere herein, handle assembly 16 includes adjustment collar 38, adjustment handle 40, actuation handle 46, and stroke regulator 48.

Adjustable length medical instrument assembly 10 may further include a tubular protective sheath 19 having a proximal end 19a (see FIGS. 1, 4) attached to and extending from adjustment handle 40 to a distal end 19b proximate tissue piercing distal end 26 of needle 20. Sheath 19 is a tubular structure in which flexible guidewire 18 and needle 20 are housed. Needle 20 is adapted to translate with respect to sheath 19 and may extend out of the open distal end 19b of sheath 19. Sheath 19 serves to cover needle 20 to protect the physician or other user of adjustable medial instrument 10 from accidental pricks by tissue piercing distal end 26 of needle 20.

Needle 20 and flexible guidewire 18 are adapted to be inserted into a working channel of a catheter. Handle assembly 16 of adjustable length medical instrument assembly 10 is adapted to be releasably attached to the catheter. As described more fully elsewhere herein, needle 20 is adapted to extend out of the catheter to pierce a target tissue. To assist a physician or other user in knowing the actual extension of needle 20, handle assembly 16 is provided with at least two localization elements 60a, 60b whose positions and orientations (POSE) in three-dimensional space can be tracked and compared by a navigation system 70 (see FIG. 6) as will be described more fully elsewhere herein.

Figure 1:
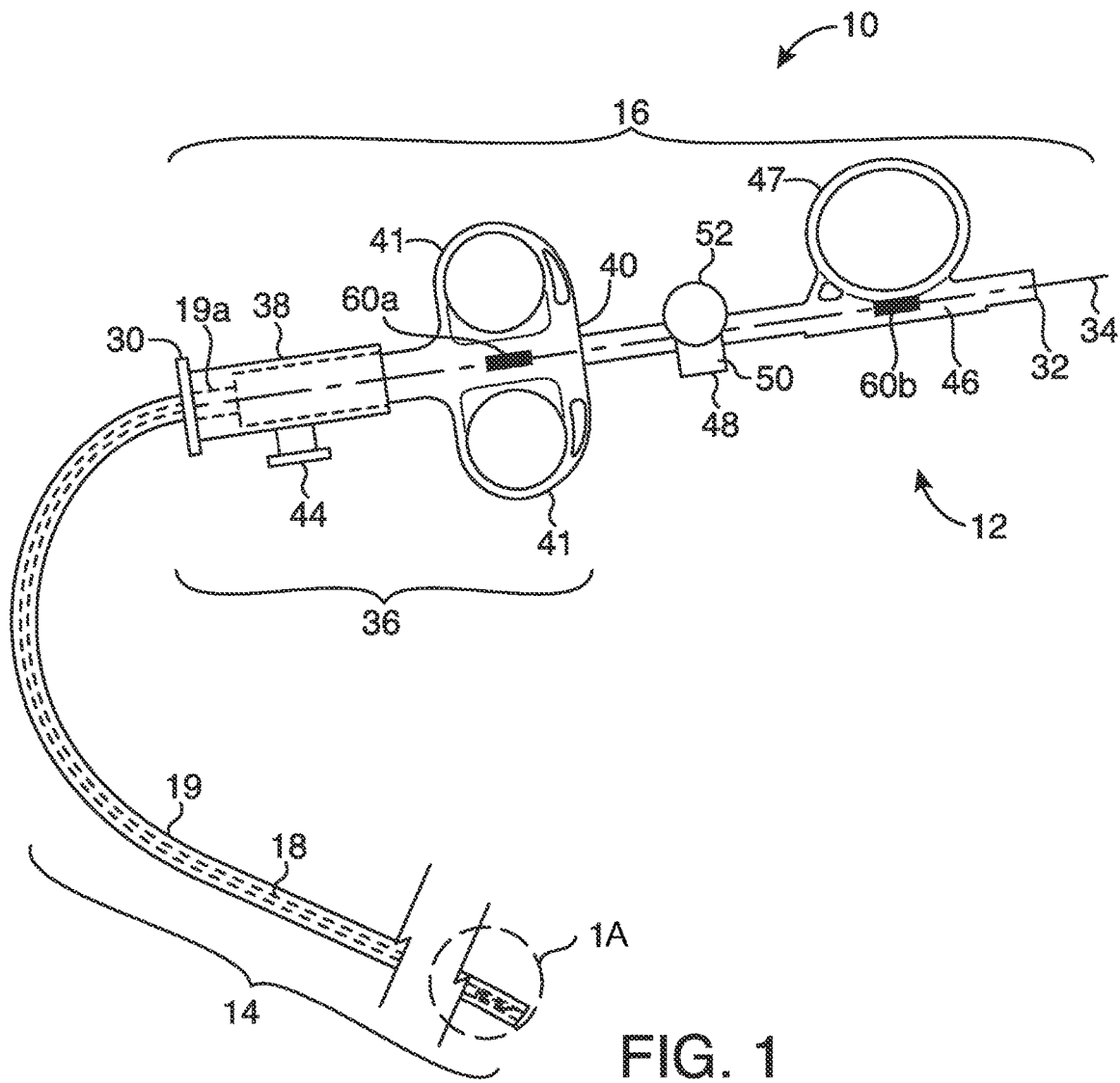
FIG. 1 is a top view of an adjustable length medical instrument assembly according to a first embodiment of the invention.
Figure 1A:
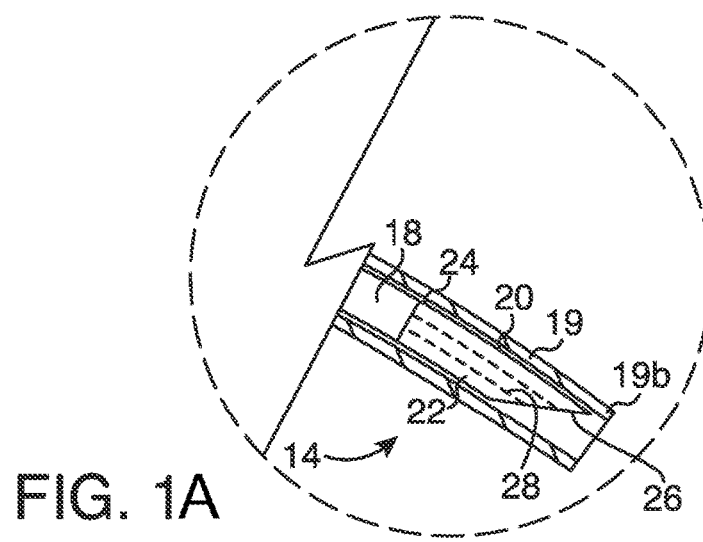
FIG. 1A is a section view of a distal end portion of an adjustable length medical instrument assembly according to an embodiment of the invention.
Figure 2:
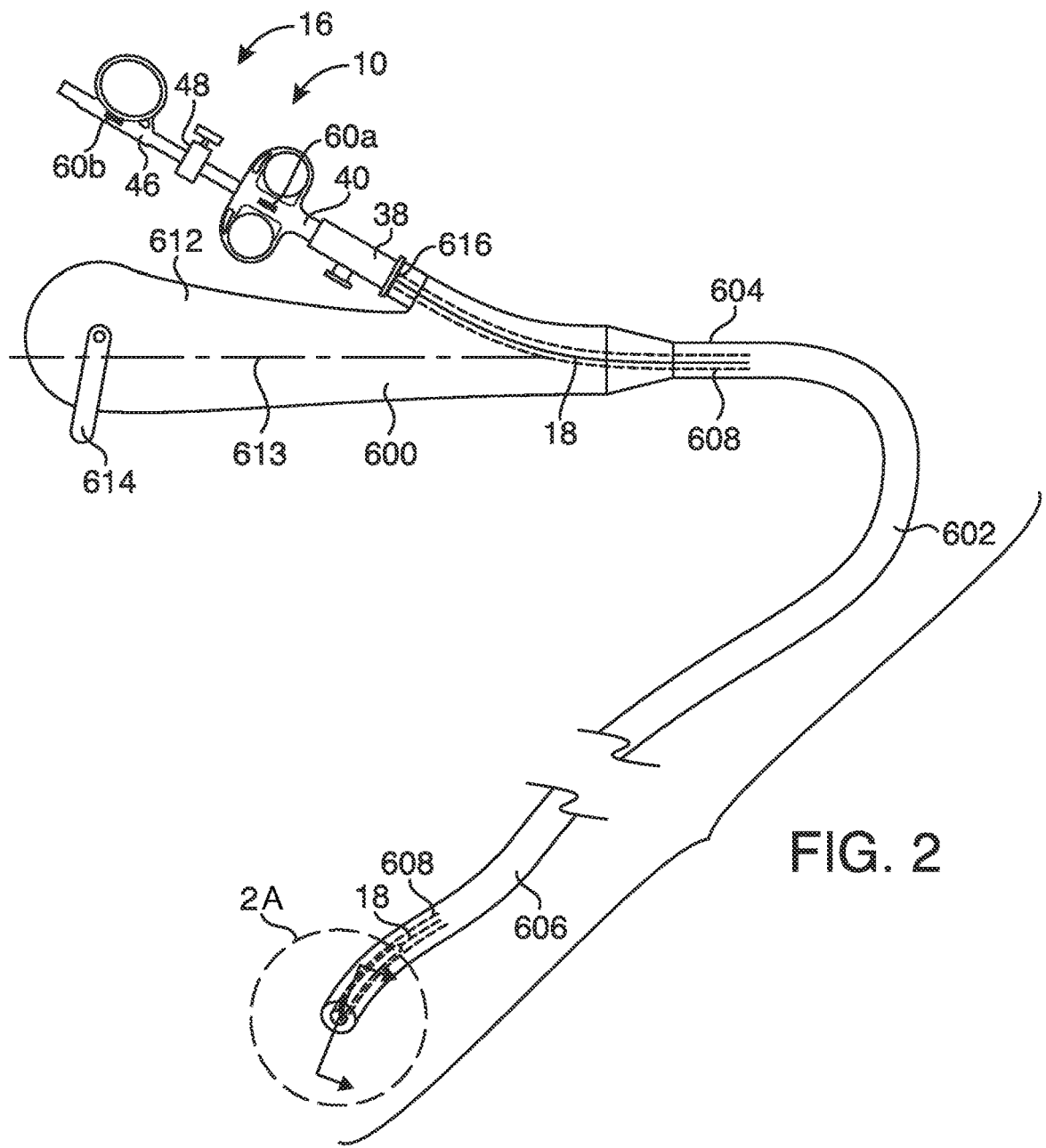
FIG. 2 is a top view of an adjustable length medical instrument assembly inserted into and connected with a catheter according to the first embodiment of the invention.
Figure 2A:
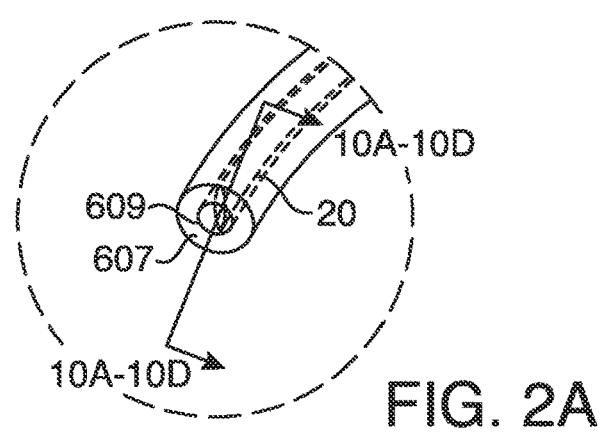
FIG. 2A is a detail view of a distal end portion of an adjustable length medical instrument assembly inserted into and connected with a catheter according to an embodiment of the invention.
Figure 4:
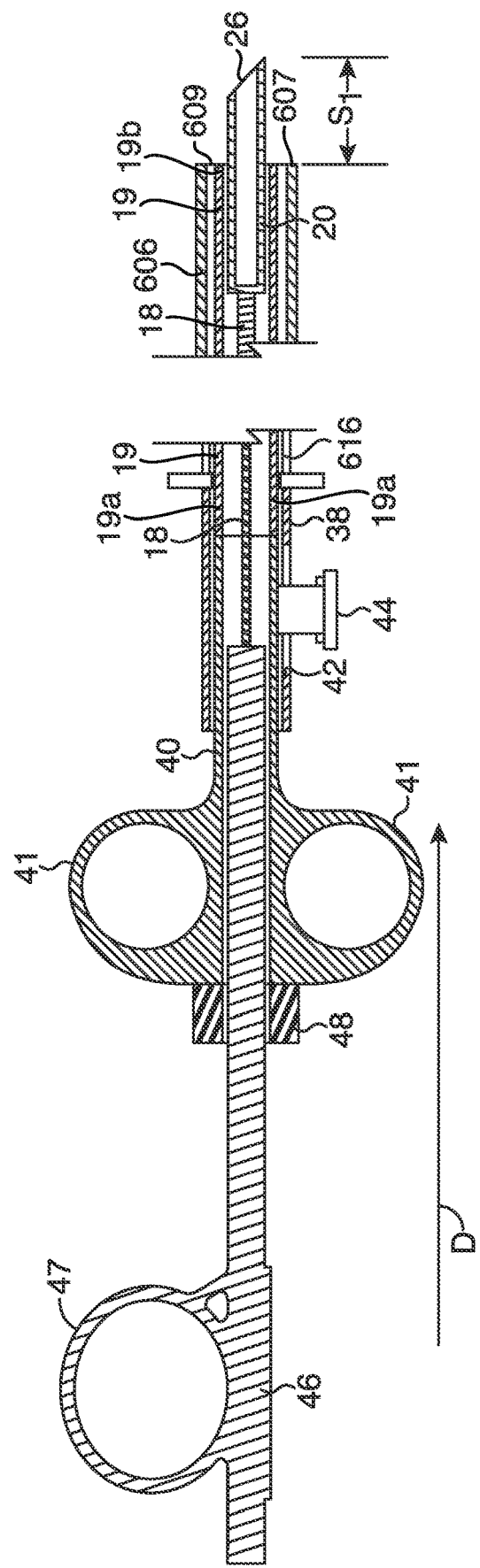
FIG. 4 is a section view of an adjustable length medical instrument assembly and a section view of a distal end portion of the adjustable length medical instrument assembly inserted into and connected with a catheter, wherein the actuation handle of the adjustable length medical instrument assembly is actuated to extend the medical instrument according to the first embodiment of the invention.

Referring now to FIG. 2, adjustable length medical instrument assembly 10 is shown in combination with a typical catheter known in the art. As described herein catheter 600 is preferably a steerable catheter; however, it will be understood that adjustable length medical instrument 10 may be used with non-steerable catheters without departing from the scope of the invention. Furthermore, it should be understood that the references made to catheter, mean or include a catheter, an endoscope, and/or a bronchoscope. Accordingly, it will be understood that adjustable length medical instrument 10 may be used with a catheter, an endoscope and/or bronchoscope without departing from the scope of the invention. Steerable catheter 600 comprises an elongate flexible shaft 602 having a proximal end portion 604, a distal end portion 606 terminating in tip 607, and one or more working channels 608 extending from proximal end portion 604 to an exit 609 proximate tip 607. Steerable catheter 600 further comprises handle 612 attached to the proximal end portion 604 of elongate flexible shaft 602. Handle 612 of steerable catheter 600 includes steering actuator 614 wherein distal end portion 606 is moved "up" and "down" relative to proximal end portion 604 by manipulating steering actuator 614 "up" and "down," respectively. Additionally, distal end portion 606 is moved "left" and "right" relative to proximal end portion 604 by rotating handle 612 "left" and "right," respectively, about handle longitudinal axis 613. It will be understood that steering actuator 614 and handle 612 are connected to a steering mechanism (not shown) on the inside of steerable catheter 600 which is connected to distal end portion 606 of elongate flexible shaft 602 for causing the deflection in distal end portion 606. Port 616, disposed on handle 612, provides access to working channel(s) 608 in elongate flexible shaft 602 of steerable catheter 600, such that needle 20 and flexible guidewire 18 may be inserted into working channel(s) 608 through port 616. Handle assembly 16 may be releasably attached to port 616 of steerable catheter 600. As described more fully elsewhere herein, adjustable length medical instrument assembly 10 may be adjusted to position needle 20 proximate exit 609 of steerable catheter 600.

Adjustable length medical instrument 10, in combination with steerable catheter 600, may be used to gain access to, manipulate, remove, sample or otherwise treat tissue within the body including, but not limited to, for example, heart or lung tissue.

Referring again to FIG. 1 and to FIGS. 3A, 3B, and 3C, additional components of adjustable length medical instrument assembly 10 are described in greater detail. Depending on the lengths of flexible guidewire 18, sheath 19, and needle 20 of adjustable length medical instrument assembly 10 and the length of elongate flexible shaft 602 of steerable catheter 600, distal end 19b of sheath 19, and tissue piercing end 26 of needle 20 may extend past the exit 609 of steerable catheter 600 when needle 20 should be at the nominal or un-extended position. To account for these length differences and to control the nominal position of distal end 19b of sheath 19 and tissue piercing end 26 of needle 20 within steerable catheter 600, the length of adjustable length medical instrument assembly 10 can be adjusted by adjusting handle assembly 16. Handle assembly 16 extends from a first end 30 to a second end 32 along longitudinal axis 34. Handle assembly 16 includes adjustment mechanism 36 proximate first end 30 and actuation handle 46 proximate second end 32.

Adjustment mechanism 36 is used to control the nominal position of distal end 19b of sheath 19 and tissue piercing end 26 of needle 20 within steerable catheter 600. Specifically, adjustment mechanism 36 includes adjustment collar 38 which is adapted to be releasably connected to a port 616 of steerable catheter 600 and adjustment handle 40 which is slidably engaged with adjustment collar 38. That is, adjustment handle 40 may be translated along longitudinal axis 34 with respect to adjustment collar 38 to control or set the nominal position of sheath 19 and needle 20 within steerable catheter 600. Adjustment handle 40 may include one or more finger holds 41 through which a physician or other user may insert their finger(s) to aid in operation of adjustable length medical instrument assembly 10. As shown in FIGS. 3A, 3B, and 3C, adjustment collar 38 includes a slot 42 along which an adjustment knob 44 affixed to adjustment handle 40 may slide. Adjustment knob 44 is loosened to allow translation of adjustment handle 40 along longitudinal axis 34 with respect to adjustment collar 38. Conversely, adjustment knob 44 is tightened to prevent translation of adjustment handle 40 along longitudinal axis 34 with respect to adjustment collar 38.

As shown in FIG. 3A, adjustment handle 40 is in a location with respect to adjustment collar 38 such that tissue piercing end 26 of needle 20 is at exit 609 of steerable catheter 600. This is the preferred nominal position of needle 20; tissue piercing end 26 of needle 20 does not extend past exit 609 (see FIG. 3B) nor is tissue piercing end 26 of needle 20 retracted into working channel 608 of steerable catheter 600 (see FIG. 3C). As represented in FIG. 3A, this nominal position is position A showing the position of adjustment knob 44 within slot 42. FIG. 3B illustrates how when adjustment handle 40 is moved along longitudinal axis 34 such that adjustment knob 44 is at position B, tissue piercing end 26 of needle 20 is past exit 609 of steerable catheter 600. FIG. 3C illustrates how when adjustment handle 40 is moved along longitudinal axis 34 such that adjustment knob 44 is at position C, distal end 19b of sheath 19 and tissue piercing end 26 of needle 20 are retracted into working channel 608 of steerable catheter 600. That is, tissue piercing end 26 of needle 20 is a distance away from exit 609 into working channel 608 of steerable catheter 600. Accordingly, depending on the differences in lengths of the flexible guidewire 18 and needle 20 and the length of elongate flexible shaft 602, adjustment handle 40 may be moved along longitudinal axis 34 and adjustment knob 44 may be secured in any location along slot 42 to control the nominal position of tissue piercing end 26 of needle 20.

While adjustment mechanism 16 controls the nominal position of distal end 19b of sheath 19 and tissue piercing end 26 of needle 20, actuation handle 46 of handle assembly 16 is adapted to extend tissue piercing end 26 of needle 20 past exit 609 of steerable catheter during a medical procedure. Actuation handle 46 may include one or more finger holds 47 through which a physician or other user may insert their finger(s) to aid in extension of tissue piercing distal end 26 of needle 20. Now with reference to FIGS. 1 and 4, actuation handle 46 is proximate second end 32 of handle assembly 16 and is slidably engaged with adjustment handle 40. That is, actuation handle 46 may be translated along longitudinal axis 34 with respect to adjustment handle 40. Flexible guidewire 18 is attached to actuation handle 46 and serves to mechanically couple needle 20 to actuation handle 46. Therefore, translation of actuation handle 46 with respect to adjustment handle 40 in the direction of arrow D (see FIG. 4) results in a coincident and coextensive translation of flexible guidewire 18 and needle 20 attached thereto. To control the translation (or extension, or stroke) of needle 20 out of exit 609 of steerable catheter 600, a needle extension or stroke regulator 48 (also known as a safety ring) is affixed to actuation handle 46. The movement of actuation handle 46, and therefore any further extension of tissue piercing end 26 of needle 20, is stopped when stroke regulator 48 contacts adjustment handle 40.

With continued reference to FIGS. 1, 3A-3C, and 4, stroke regulator 48 may include a ring 50 which is slidably engaged with actuation handle 46 and adjustment knob 52 on ring 50. Adjustment knob 52 is loosened to allow translation of stroke regulator 48 along longitudinal axis 34 with respect to actuation handle 46. Conversely, adjustment knob 52 is tightened to prevent translation of stroke regulator 48 along longitudinal axis 34 with respect to actuation handle 46. Stroke regulator 48 may be set or secured at a variety of locations on actuation handle 46 along longitudinal axis 34 to regulate or limit the amount of translation (or extension, or stroke) of tissue piercing end 26 of needle 20 out of exit 609 of steerable catheter 600. Stroke regulator 48 may be set to allow from about 0 mm to about 100 mm of extension of needle 20 out of exit 609 of steerable catheter 600 (e.g., about 0 mm, about 10 mm, about 20 mm, about 30 mm, about 40 mm, about 50 mm, about 60 mm, about 80 mm, about 90 mm, about 100 mm). The extension of tissue piercing end 26 of needle 20 is preferably set to a desired "maximum" so that needle 20 will not extend beyond a desired point when in the patient. For example, if the target tissue that a physician or other user wishes to interact with is only 10 mm in diameter, the physician or other user may set the stroke extension of tissue piercing end 26 of needle 20, using stroke regulator 48, to 10 mm so that tissue piercing end 26 of needle 20 does not extend into tissue(s) other than the target. Extension markings (not shown) may be provided on actuation handle 46 to assist in the physician or other user in positioning stroke regulator 48 for the desired extension.

Accordingly, it is important for a physician or other user to be able to set the maximum extension of needle 20 as provided by stroke regulator 48. However, it is also beneficial for the physician or other user to know the actual extension or stroke of needle 20 out exit 609 of steerable catheter 600. While the physician or other user can look at the extension markings to estimate the amount of extension, the physician or other user may not know the exact extension of needle 20 by looking at such markings alone. To assist the physician or other user in knowing the actual extension of needle 20, handle assembly 16 is provided with at least two localization elements 60a, 60b whose positions and orientations (POSE) in three-dimensional space can be tracked and compared by a navigation system 70. Now with reference to FIGS. 1, 2, 3A-3C, and 5, a first localization element 60a may be affixed or attached to adjustment handle 40 and a second localization element 60b may be affixed to actuation handle 46. Preferably, first and second localization elements 60a, 60b are releasably affixed or attached to adjustment handle 40 and actuation handle 46. For example, as shown in FIGS. 5A, 5AA, 5B, and 5BB, adjustment and actuation handles 40, 46 may have semi-cylindrical slots or grooves 54. Correspondingly, first and second localization elements 60a, 60b may be cylindrical in shape and therefore may be snapped or slid into semi-cylindrical slots or grooves 54. While first localization element 60a is preferably affixed to adjustment handle 40, it will be understood that, in other embodiments, for example, first localization element 60a may be affixed to adjustment collar 38 without departing from the scope of the invention. Additionally, while second localization element 60b is preferably affixed to actuation handle 46 as shown in FIGS. 5A and 5AA, it will be understood that, in other embodiments, for example, second localization element 60b may be affixed to stroke regulator 48 as shown in FIGS. 5C and 5CC without departing from the scope of the invention.

In alternative embodiments, first and second localization elements 60a, 60b may be attached to adjustment handle 40, actuation handle 46, adjustment collar 38, and/or stroke regulator 48 by other attachment devices including, but not limited to, adhesives (e.g., tape, glue, cement, etc.), screws, clips, hook-and-loop type fasteners or straps (e.g., Velcro®), bands (e.g., rubber bands, elastic bands, etc.), cable ties, (e.g., zip ties, tie-wrap, etc.), shrink wrap, and any other attachment devices known in the art. While localization elements are preferably releasably affixed to handle assembly 16 of adjustable length medical instrument assembly 10, it will be understood that in other embodiments, for example, first and second localization elements 60a, 60b may be permanently affixed to handle assembly 16, respectively.

Typical adjustable length medical instruments are single-use disposable "dumb" instruments. That is, they do not include any sensors for tracking their location and operation. By providing adjustable length medical instrument assembly 10 with slots or grooves 54 into which reusable localization elements 60a, 60b may be releasably affixed, adjustable length medical instrument assembly 10 is a "smart" instrument. Furthermore, by incorporating localization elements 60a, 60b on handle assembly 16 of adjustable length medical instrument assembly 10, needle 20 can be smaller in diameter than a needle that includes a localization element. Placement of localization elements 60a, 60b on handle assembly 16 additionally allows the use of larger and/or lower cost localization elements than the much smaller localization elements that would be required if located on a needle.

The position and orientation (POSE) of first and second localization elements 60a, 60b are detectable by navigation system 70 as described more fully below. The first and second localization elements 60a, 60b may be connected by wires 62 to navigation system 70; in alternative embodiments, first and second localization elements 60a, 60b may be wirelessly connected to navigation system 70. Preferably, first and second localization elements 60a, 60b are electromagnetic (EM) coil sensors. In certain embodiments, first and second localization elements 60a, 60b are six (6) degree of freedom (6DOF) EM sensors. In other embodiments, first and second localization elements 60a, 60b are five (5) degree of freedom (5DOF) EM sensors. In other embodiments, first and second localization elements 60a, 60b comprise other localization devices such as radiopaque markers that are visible via fluoroscopic imaging and echogenic patterns that are visible via ultrasonic imaging. In yet other embodiments, first and second localization elements 60a, 60b may be, for example, infrared light emitting diodes, and/or optical passive reflective markers. First and second localization elements 60a, 60b may also be, or be integrated with, one or more fiber optic localization (FDL) devices.

As shown in FIG. 6, navigation system 70 comprises a processor 72 having memory component 74, input/output (I/O) component 78, and localization device 76. Navigation system 70 also includes display 80, electromagnetic field generator 82, and/or user interface device(s) 84 (e.g., keyboard, mouse). Examples of suitable navigation systems are the SPiNView® Thoracic Navigation System and the ig4™ IR System, commercially available from Veran Medical Technologies, Inc. (St. Louis, Missouri. USA).

Processor 72 of navigation system 70 includes a processor-readable medium storing code representing instructions to cause the processor 72 to perform a process. Processor 72 can be, for example, a commercially available personal computer, or a less complex computing or processing device that is dedicated to performing one or more specific tasks. For example, processor 72 can be a terminal dedicated to providing an interactive graphical user interface (GUI) on optional display 80. Processor 72, according to one or more embodiments of the invention, can be a commercially available microprocessor. Alternatively, processor 72 can be an application-specific integrated circuit (ASIC) or a combination of ASICs, which are designed to achieve one or more specific functions, or enable one or more specific devices or applications. In yet another embodiment, processor 72 can be an analog or digital circuit, or a combination of multiple circuits.

Additionally, processor 72 can include memory component 74. Memory component 74 can include one or more types of memory. For example, memory component 74 can include a read only memory (ROM) component and a random access memory (RAM) component. Memory component 74 can also include other types of memory that are suitable for storing data in a form retrievable by processor 72. For example, electronically programmable read only memory (EPROM), erasable electronically programmable read only memory (EEPROM), flash memory, as well as other suitable forms of memory can be included within the memory component. Processor 72 can also include a variety of other components, such as for example, coprocessors, graphic processors, etc., depending upon the desired functionality of the code.

Processor 72 can store data in memory component 74 or retrieve data previously stored in memory component 74. The components of processor 72 can communicate with devices external to processor 72 by way of input/output (I/O) component 78. According to one or more embodiments of the invention, I/O component 78 includes a variety of suitable communication interfaces. For example, I/O component 78 can include, for example, wired connections, such as standard serial ports, parallel ports, universal serial bus (USB) ports, S-video ports, local area network (LAN) ports, small computer system interface (SCSI) ports, and so forth. Additionally, I/O component 78 can include, for example, wireless connections, such as infrared ports, optical ports, Bluetooth® wireless ports, wireless LAN ports, or the like. Additionally, display 80, electromagnetic field generator 82, and/or user interface device(s) 84, communicate with processor 72 via I/O component 78.

Processor 72 can be connected to a network, which may be any form of interconnecting network including an intranet, such as a local or wide area network, or an extranet, such as the World Wide Web or the Internet. The network can be physically implemented on a wireless or wired network, on leased or dedicated lines, including a virtual private network (VPN).

In general, navigation system 70 may comprise any tracking system typically employed in image guided surgery, including but not limited to, an electromagnetic tracking system. An example of a suitable electromagnetic tracking subsystem is the AURORA electromagnetic tracking system, commercially available from Northern Digital Inc. (Waterloo, Ontario Canada). In one embodiment, navigation system 70 may include an electromagnetic tracking system, typically comprising an electromagnetic (EM) field generator 82 that emits a series of electromagnetic fields designed to engulf first and second localization elements 60a, 60b. In certain embodiments, for example, first and second localization elements 60a, 60b are electromagnetic coils that receive an induced voltage from electromagnetic (EM) field generator 82, wherein the induced voltage is monitored and translated by localization device 76 into a coordinate position in three-dimensional space of first and second localization elements 60a, 60b (see $(X_1, Y_1, Z_1)$ for 60a, and $(X_2, Y_2, Y_2)$ for 60b in FIG. 4). In certain embodiments, first and second localization elements 60a, 60b are electrically coupled to twisted pair conductors to provide electromagnetic shielding of the conductors. This shielding prevents voltage induction along the conductors when exposed to the magnetic flux produced by the electromagnetic field generator.

Accordingly, localization device 76 may be, for example, an analog to digital converter that measures voltages induced onto first and second localization elements 60a, 60b in the field generated by EM field generator 82; creates a digital voltage reading; and maps that voltage reading to a metric positional measurement based on a characterized volume of voltages to millimeters from electromagnetic field generator 82. Position data associated with first and second localization elements 60a, 60b may be transmitted or sent to localization device 76 continuously during a medical procedure. Thus, the position of first and second localization elements 60a, 60b (see $(X_1, Y_1, Z_1)$ for 60a, and $(X_2, Y_2, Y_2)$ for 60b in FIG. 4) may be captured at given instants in time during the medical procedure. The distance, range, acceleration, and/or speed between first and second localization elements 60a, 60b may then be determined and various algorithms may be used to analyze and compare the distance between first and second localization elements 60a, 60b at given instants in time. Consequently, navigation system 70 may determine the relative distance between first and second localization elements 60a and 60b to determine the actual translation, extension, or stroke $(S_1)$ of tissue piercing end 26 of needle 20 out of exit 609 of steerable catheter 600.

To aid in the determination of the actual translation, extension, or stroke (S1) of tissue piercing end 26 of needle 20, the positions of one or both of first localization element 60a and second localization element 60b may be "zeroed out" or initialized prior to any extension of tissue piercing end 26 of needle. For example, after the nominal position of tissue piercing end 26 of needle 20 is set by adjusting adjustable handle 40 with respect to adjustment collar 38 (as shown in FIGS. 3A-3C) and actuation handle 46 is maintained in a location such that tissue piercing end 26 of needle 20 is not extended, the physician or other user may set on navigation system 70 the positions of one or both of first localization element 60a and second localization element 60b as initial positions or zero extension positions. This "zeroing out" can be performed to indicate to navigation system 70 that there is no extension of tissue piercing end 26 of needle 20. Accordingly, after zeroing out, relative movement between first and second localization elements 60a, 60b can indicate the actual translation, extension, or stroke $(S_1)$ of tissue piercing end 26 of needle 20 out of exit 609 of steerable catheter 600. Zeroing out or initialization of the position of first and/or second localization elements 60a, 60b may be particularly beneficial if first localization element 60a is affixed to adjustment collar 38 instead of adjustment handle 40.

The actual translation, extension, or stroke $(S_1)$ of tissue piercing end 26 of needle 20 may be displayed to physician or other user on display 80 of navigation system 70. In various embodiments, the extension or stroke of tissue piercing end 26 of needle 20 may be displayed as a number on display 80. Based on the displayed extension or stroke, the user may then determine whether to continue to extend tissue piercing end 26 of needle 20, to maintain the extension of tissue piercing end 26 of needle 20, or to retract tissue piercing end 26 of needle 20 back into steerable catheter 600.

Alternative embodiments of an adjustable length medical instrument assembly of the disclosure is illustrated in FIGS. 7 and 8 are described below. Some features one or more of adjustable length medical instrument assembly 10, 110, 210 are common to one another and, accordingly, descriptions of such features in one embodiment should be understood to apply to other embodiments. Furthermore, particular characteristics and aspects of one embodiment may be used in combination with, or instead of, particular characteristics and aspects of another embodiment.

With reference to FIG. 7, actuation handle 146 of adjustable length medical instrument assembly 110 includes proximal end 146a, distal end 146b, and lumen 146c extending therebetween. Additionally, adjustable length medical instrument assembly 110 further includes flexible tubing 118 extending from proximal end 146a of actuation handle 146 to proximal end 24 of needle 20. Flexible tubing 118 serves to mechanically couple needle 20 to actuation handle 146. Flexible tubing 118 is preferably hollow, having lumen 118a extending therebetween. Lumen 146c, lumen 118a, and lumen 28 are all in fluid communication with one another which permits material (e.g., tissue, fluid, medicine, devices, etc.) to be passed into or removed out of the patient. As is known in the art, a luer lock fitting or other type of fitting for attaching a syringe may be at distal end 146b of actuation handle to which a syringe may be secured.

With reference to FIG. 8, yet another alternative embodiment of adjustable length medical instrument assembly 210 is described. Actuation handle 246 of adjustable length medical instrument assembly 210 includes proximal end 246a, distal end 246b, and lumen 246c extending therebetween. Additionally, adjustable length medical instrument assembly 210 further includes flexible needle 220 extending from proximal end 246a of actuation handle 246 to tissue piercing distal end 26 of needle 220. That is, instead of the needle being mechanically coupled to the actuation handle by a flexible guidewire or flexible tubing, flexible needle 220 extends from proximate proximal end 12 to distal end 14 of adjustable length medical instrument assembly 210. Much like flexible tubing 118, flexible needle 220 is preferably hollow, having lumen 228 extending from proximal end 224 of needle 220 affixed to proximal end 246a of actuation handle 246 to tissue piercing distal end 26 of needle 220. Lumen 246c and lumen 228 are in fluid communication with one another which permits material (e.g., tissue, fluid, medicine, devices, etc.) to be passed into or removed out of the patient. As is known in the art, a luer lock fitting or other type of fitting for attaching a syringe may be at distal end 246b of actuation handle to which a syringe may be secured.

In various embodiments, needle 20, 220 may be highly bendable or flexible. As shown in FIGS. 9A and 9B, needle 20, 220, for example, may include cuts 22a in outer wall 22 to facilitate or increase bending or flexure of needle 20, 220. In various embodiments, for example, cuts may be spiral or helical cuts. In other embodiments, for example, cuts may be in any pattern on outer wall 22 which facilitates or increases bending or flexure of needle 20, 220. Preferably, cuts are made using a laser. In other embodiments, for example, needle 20, 220 may be made or formed of flexible materials including, but not limited to, nitinol, stainless steel, or other metals or alloys thereof, and plastics. Preferably, flexible needle 220 is formed of nitinol.

In various embodiments, with reference to FIGS. 10A-10D, a third localization element 60c may be proximate the tissue piercing distal end 26 of needle 20, 220 to provide trajectory information of needle 20, 220. The position and orientation of the localization element 60c may be tracked by navigation system 70, and may be used in addition to the actual translation, extension, or stroke ($S_1$) of needle 20, 220 to display on display 80 the trajectory of needle 20, 220. Using position and orientation information from localization element 60c, navigation system 70 may display on display 80 a simulated needle extension superimposed on pre-acquired images depicting a portion of the patient including the tissue(s) desired to be targeted by needle 20, 220. Alternatively, navigation system 70 may be able to display on display 80 a simulated needle extension superimposed on a virtual representation of the patient including the tissue(s) desired to be targeted by needle 20, 220. Therefore, the physician or other user may be presented with a real-time simulated display of needle 20 intercepting the target tissue(s).

To determine trajectory information, one or more localization elements 60c that are detectable by a navigation system 70 may be disposed proximate the tissue piercing distal end 26 of needle as shown in FIGS. 10A-10D. Accordingly, the position and orientation (POSE) of localization elements 60c are tracked by localization device 76 of navigation system 70 and the trajectory of needle 20 may be determined therefrom.

The one or more localization elements 60c may be connected by wire 61 to navigation system 70; in alternative embodiments, the one or more localization elements 60c may be wirelessly connected to navigation system 70. In certain embodiments, localization elements 60c comprise six (6) degree of freedom (6DOF) electromagnetic coil sensors. In other embodiments, localization elements 60c comprise five (5) degree of freedom (5DOF) electromagnetic coil sensors. In other embodiments, localization elements 60c comprise other localization devices such as radiopaque markers that are visible via fluoroscopic imaging and echogenic patterns that are visible via ultrasonic imaging. In yet other embodiments, localization elements 60c may be, for example, infrared light emitting diodes, and/or optical passive reflective markers. Localization elements 60c may also be, or be integrated with, one or more fiber optic localization (FDL) devices.

As shown in FIG. 10A, in various embodiments, for example, localization element 60c is located on or in distal end portion 606 proximate tip 607 of elongate flexible shaft 602 of catheter 600. In other embodiments, for example, as shown in FIG. 10B, localization element 60c is located on or in distal end 19b of sheath 19 of adjustable length medical instrument 10, 110, 210. As shown in FIG. 10C, in yet other embodiments, for example, localization element 60c is located on or in needle 20, 220 proximate tissue piercing distal end 26. In yet other embodiments, for example, as shown in FIG. 10D, localization element 60c is located on or in the tip 18b of flexible guidewire 18a which may be inserted through lumen 146c of actuation handle 146 and lumen 118a of flexible tubing 118 of adjustable length medical instrument 110 to proximate tissue piercing distal end 26 of needle 20 or through lumen 246c of actuation handle 246 and lumen 228 of needle 220 of adjustable length medical instrument 210 to proximate tissue piercing distal end 26 of needle 220.

In various embodiments, localization element 60c may be integrally formed with elongate flexible shaft 602 of catheter 600, sheath 19, needle 20, 220, and/or flexible guidewire 18a. In other embodiments, localization element 60c may be affixed or adhered to elongate flexible shaft 602 of catheter, sheath 19, needle 20, 220, and/or flexible guidewire 18a. For example, localization element 60c may be affixed to needle 20, 220 by a length of heat shrink tubing. In other embodiments, localization element 60c may be affixed or adhered to elongate flexible shaft 602 of catheter 600, 2600, 3600, sheath 19, needle 20, 220, and/or flexible guidewire 18a by any type of bio-compatible adhesives and/or tapes known in the art. By including localization element 60c on sheath 19, needle 20, 220, and/or on flexible guidewire 18a, catheter 600 may be a cheaper non-navigated catheter.

The use of flexible guidewire 18a shown in FIG. 10D (with or without localization element 60c), may be beneficial in the use of needle 20, 220 where needle 20, 220 is a highly flexible needle or includes cuts to increase flexibility of needle 20, 220 (see 22a in FIGS. 9A, 9B). Flexible guidewire 18a may serve two purposes. First, where needle 20, 220 is bendable or flexible as described above, flexible guidewire 18a may provide stiffness to needle 20, 220 as it is being navigated to the target location (see FIG. 11A) through an airway 400. Flexible guidewire 18a may then be retracted a distance, for example, about 10 mm to about 20 mm, inside lumen 28, 228 of needle 20, 220 to allow needle 20, 220 to bend around a tight turn in an airway 400, for example (see FIG. 11B). After needle 20, 220 passes around the turn, flexible guidewire 18a may then be re-extended so that tip 18b is proximate tissue piercing distal end 26 of needle 20, 220 (see FIG. 11C). Second, as described above, localization element 60c on flexible guidewire 18a allows the tissue piercing distal end 26 of needle 20, 220 to be tracked. Once needle 20, 220 has been navigated proximate the desired target, flexible guidewire 18a may be removed from lumens 146c, 118a of adjustable length medical instrument assembly 110 or lumens 246c, 228 of adjustable length medical instrument assembly 210 and a sample of the target tissue may be taken through needle 20, 220 via aspiration and/or suction.

Although adjustable length medical instrument assembly 10 has been described with the use of needle 20, it will be understood that in alternative embodiments an adjustable length medical instrument assembly 10 may include other medical instruments alternative to needle 20. Such alternative medical devices, include but are not limited to, stents, ablation probes, biopsy devices, forceps devices, brushes, augers, stylets, pointer probes, radioactive seeds, implants, energy delivery devices, therapy delivery devices, devices to deliver energy activated substances (e.g., porfimer sodium) and energy associated devices, radiofrequency (RF) energy devices, cryotherapy devices, laser devices, microwave devices, diffuse infrared laser devices, steam ablation devices, etc. Furthermore, alternative medical instruments may also include a fiber optic cable, a radial endobronchial ultrasound (EBUS) device, optical coherence tomography (OCT) device, or other known imaging devices for visualization and/or diagnosis of the target tissue. Yet another alternative medical instrument may include a microscopy device for visualization and/or diagnosis of the target tissue by evaluating the target tissue at the cellular level.

Additionally, various embodiments that utilize needle 220 with lumen 228, various medical instruments may be inserted into lumen 228 including but not limited to, stents, ablation probes, biopsy devices, forceps devices, brushes, augers, stylets, pointer probes, radioactive seeds, implants, energy delivery devices, therapy delivery devices, devices to deliver energy activated substances (e.g., porfimer sodium) and energy associated devices, radiofrequency (RF) energy devices, cryotherapy devices, laser devices, microwave devices, diffuse infrared laser devices, steam ablation devices, etc. Furthermore, a fiber optic cable, a radial endobronchial ultrasound (EBUS) device, optical coherence tomography (OCT) device, or other known imaging devices may be inserted into lumen 228 of needle 220 for visualization and/or diagnosis of the target tissue. Additionally, a microscopy device may be inserted into lumen 228 of needle 220 for visualization and/or diagnosis of the target tissue by evaluating the target tissue at the cellular level.

Additionally, although an adjustable length medical instrument assembly 10 has been described, it will be understood that in alternative embodiments, medical instrument assemblies with or without an adjustable length feature may include first and second localization elements for tracking the extension of a medical instrument without departing from the scope of the invention. For example, in various embodiments, a medical instrument assembly may include a first handle portion and a second handle portion, wherein the second handle portion is slidably engaged with the first handle portion. Translation of the second handle portion with respect to the first handle portion may cause a coincident and coextensive movement of a medical instrument mechanically coupled to the second handle portion. A first localization element may be attached to the first handle portion and a second localization element may be attached to the second handle portion wherein the amount of translation of the medical instrument is adapted to be determined by calculating the distance between the first localization element and the second localization element.

Thus, there has been shown and described novel methods and apparatuses of a medical instrument assembly having localization elements for tracking the extension of a medical instrument. It will be apparent, however, to those familiar in the art, that many changes, variations, modifications, and other uses and applications for the subject devices and methods are possible. All such changes, variations, modifications, and other uses and applications that do not depart from the spirit and scope of the invention are deemed to be covered by the invention which is limited only by the claims which follow.

The invention claimed is:
1. A medical instrument assembly comprising:
a catheter comprising an elongate flexible shaft having a proximal end portion comprising a port, an opposite distal end portion terminating in a tip, and a working channel extending from the port to an exit adjacent to the tip;
a medical device assembly at least a portion of which is adapted to be inserted into the working channel of the catheter, the medical device assembly comprising:
a handle assembly having a first end and a second end, the handle assembly comprising a first handle portion adjacent to the first end and a second handle portion adjacent to the second end, wherein the second handle portion is slidably engaged with the first handle portion, the first handle portion and the second handle portion each comprise a groove;
a first electromagnetic sensor adapted to be releasably retained in the groove of the first handle portion of the medical device assembly, and a second electromagnetic sensor adapted to be releasably retained in the groove of the second handle portion of the medical device assembly;
a needle, the needle having a proximal end and a distal end and defining a lumen that extends from the proximal end to the distal end, wherein the proximal end is mechanically coupled to the second handle portion and wherein a translation of the second handle portion with respect to the first handle portion causes a movement of the medical instrument, the movement corresponding to an extension of the distal end of the needle from the tip;
a medical instrument, the medical instrument being positioned within the lumen for advancement therethrough; and a navigation system, the navigation system comprising:
a processor, the processor adapted to determine the extension of the distal end of the needle relative to the tip by calculating the distance between the first electromagnetic sensor and the second electromagnetic sensor based on the first position of the first electromagnetic sensor and the second position of the second electromagnetic sensor;
an electromagnetic field generator for inducing the voltage in the first electromagnetic sensor and the second electromagnetic sensor, the voltage being an output,
a localization device for measuring the voltages induced into the first and second electromagnetic sensors and translating the measured voltages into the first and second positions, and
a display for displaying a representation of the determined amount of movement of the needle.

2. The medical instrument assembly of claim 1, wherein the first handle portion comprises an adjustment collar and an adjustment handle slidably engaged with the adjustment collar.

3. The medical instrument assembly of claim 2, wherein the first electromagnetic sensor is attached to the adjustment handle or the adjustment collar.

4. The medical instrument assembly of claim 2, further comprising a protective sheath having a proximal end affixed to and extending from the adjustment handle to a distal end adjacent to the distal end of the medical instrument.

5. The medical instrument assembly of claim 4, further comprising a third electromagnetic sensor attached to the distal end of the protective sheath.

6. The medical instrument assembly of claim 2, wherein the second handle portion comprises an actuation handle slidably engaged with the adjustment handle and a stroke regulator adjustably secured to the actuation handle to control the amount of movement of the medical instrument.

7. The medical instrument assembly of claim 1, further comprising a third electromagnetic sensor located at a distal end portion of the medical instrument.

8. The medical instrument assembly of claim 7, wherein the medical instrument is a flexible guidewire, wherein the flexible guidewire includes a tip, the third electromagnetic sensor located on or in the tip of the flexible guidewire.

9. The medical instrument assembly of claim 1, wherein the needle includes a third electromagnetic sensor.

10. The medical instrument assembly of claim 1, wherein the proximal end of the needle is mechanically coupled to the second handle portion by an elongate flexible guidewire.

11. The medical instrument assembly of claim 1, wherein the needle comprises an outer wall extending from the proximal end to the distal end and wherein at least a portion of the outer wall is cut to increase flexibility of the needle.

* * * * *